(12) United States Patent
Plishka et al.

(10) Patent No.: US 7,744,270 B2
(45) Date of Patent: Jun. 29, 2010

(54) CURABLE MATERIAL MIXING AND DELIVERY DEVICE

(75) Inventors: Michael Plishka, Lake Villa, IL (US); Randall Scott Koplin, Chicago, IL (US)

(73) Assignee: CareFusion 2200, Inc., San Diego, CA (US)

( * ) Notice: Subject to any disclaimer, the term of this patent is extended or adjusted under 35 U.S.C. 154(b) by 1146 days.

(21) Appl. No.: 11/372,642

(22) Filed: Mar. 10, 2006

(65) Prior Publication Data
US 2007/0211565 A1    Sep. 13, 2007

(51) Int. Cl.
B01F 7/00    (2006.01)
B01F 7/08    (2006.01)
B01F 15/02    (2006.01)

(52) U.S. Cl. .................. 366/189; 366/195; 366/308; 366/320

(58) Field of Classification Search .......... 366/379, 366/289, 308, 320, 189, 195
See application file for complete search history.

(56) References Cited

U.S. PATENT DOCUMENTS

| | | | |
|---|---|---|---|
| 3,752,364 A * | 8/1973 | De Vries | ...... 222/131 |
| 4,808,184 A | 2/1989 | Tepic | |
| 5,516,135 A * | 5/1996 | Christenson | ...... 280/405.1 |
| 5,588,745 A | 12/1996 | Tanaka et al. | |
| 6,176,607 B1 * | 1/2001 | Hajianpour | ...... 366/139 |
| 2002/0191487 A1 | 12/2002 | Sand | |
| 2004/0196735 A1 | 10/2004 | Barker et al. | |
| 2005/0222538 A1 * | 10/2005 | Embry et al. | ...... 604/181 |

OTHER PUBLICATIONS

European Search Report for EP Application No. 07 25 1002, completed Jul. 11, 2007, 2 pages.

* cited by examiner

*Primary Examiner*—Tony G Soohoo
(74) *Attorney, Agent, or Firm*—Brinks Hofer Gilson & Lione

(57) ABSTRACT

An apparatus and method for mixing two components and delivering the mixture to a patient. The apparatus contains a mixing chamber for mixing a liquid component and a powder component. The liquid component and powder component are mixed within the mixing chamber by rotation of a collapsible mixing element. A plunger is then advanced through the mixing chamber to force the mixture out of the mixing chamber and deliver the mixture to the patient.

17 Claims, 13 Drawing Sheets

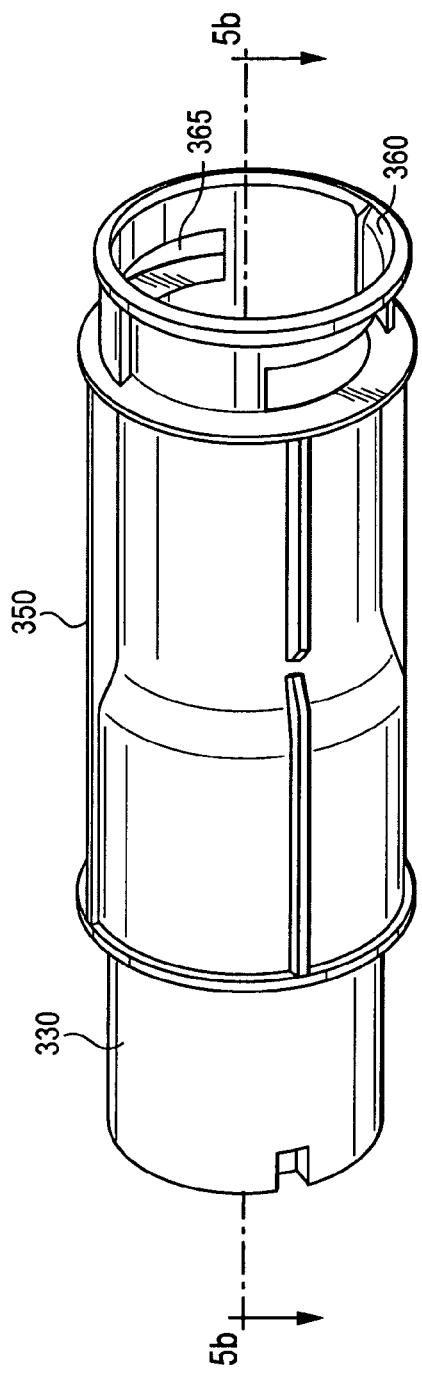
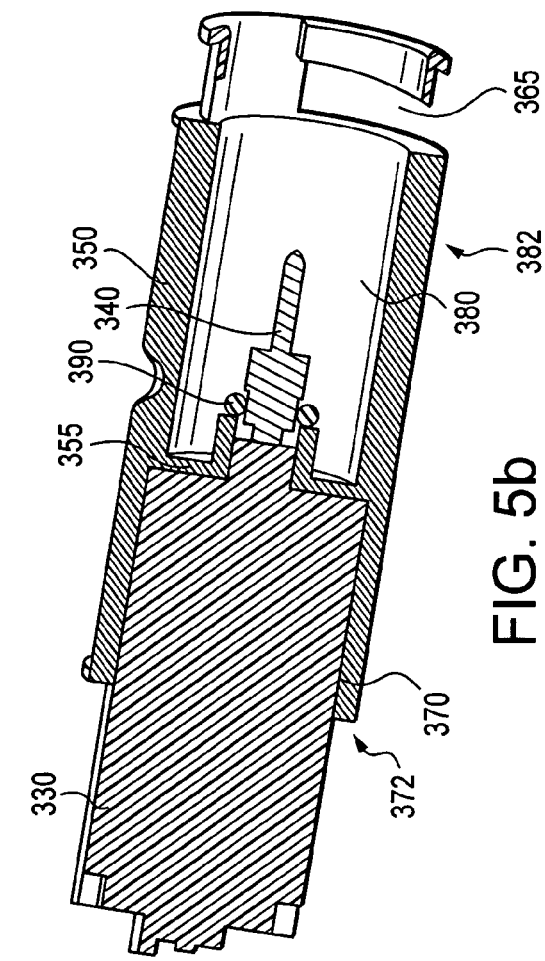
FIG. 5a
FIG. 5b

CURABLE MATERIAL MIXING AND DELIVERY DEVICE

TECHNICAL FIELD

The present invention relates to devices and methods for mixing curable materials for use with stabilizing bone structures. More particularly, it relates to devices, systems and methods for mixing the components that form the curable materials.

BACKGROUND INFORMATION

Surgical intervention at damaged or compromised bone sites has proven highly beneficial for patients, for example patients with back pain associated with vertebral damage. Bones of the human skeletal system include mineralized tissue that can generally be categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae."

During certain bone procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., polymethylmethacrylate (PMMA) or other curable material). In other procedures, percutaneous injection under computed tomography (CT) and/or fluoroscopic guidance of stabilization material into vertebral compression fractures by, for example, transpedicular or parapedicular approaches, has proven beneficial in relieving pain and stabilizing damaged bone sites. Other skeletal bones (e.g., the femur) can be treated in a similar fashion. In any regard, bone in general, and cancellous bone in particular, can be strengthened and stabilized by a palliative injection of bone-compatible curable material.

The curable material used in the above procedures is typically fashioned by mixing a liquid component and a powder component within the operating room just prior to placement of the curable material into an injector wherein the injector is then used to introduce the curable material into the patient. Curable material may be prepared by mixing a very fine cement powder, typically PMMA, with a liquid monomer, typically methylmethacrylate.

According to mixing methods of the prior art, the components of the curable material are mixed in a mixing bowl and then transferred to a delivery system, such as a syringe or other injector, to deliver the curable material to the patient. This method can delay procedures while the cement is being transferred to the delivery system and the curable material may be spilled during the transfer. The delay increases procedure time and can cause the curable material to set before the procedure is completed. Additionally, the mixing of the components creates undesirable fumes that have an offensive odor to many. The mixing of the components in an open mixing bowl exposes the operating room to obnoxious fumes. Further, mixing is typically done by hand by the physician. Hand mixing can be tedious and unpredictable, resulting in potentially poor quality curable material.

There exists a need in the medical device field for an improved curable material mixing and delivery device. The present invention provides an efficient device and method for mixing and delivering components of a curable material.

BRIEF SUMMARY

One aspect of the present invention is directed to a device for mixing two components and dispensing a mixture. The device has a mixer section that defines a mixing chamber having a first end and a second end. The device also has a mixing element holder at the first end of the mixing chamber wherein the mixing element holder defines a passageway between the mixing chamber and the exterior of the mixing chamber. The device further has a collapsible mixing element connected with the mixing element holder and operative to mix a first component and a second component within the mixing chamber. The device also has a plunger operative to substantially seal against an interior surface of the mixing chamber wherein the collapsing mixing element collapses at the first end as the plunger is advanced from the second end to the first end and the mixture is dispensed through the passageway in the mixing element holder.

In another aspect of the present invention, a device for mixing two components is provided. In this embodiment, the device has a mixing barrel defining a mixing chamber. The device also has a liquid component introduction port on the mixing barrel for introducing a liquid component into the mixing chamber. The device further has a spring holder within the mixing chamber. The device also has a spring connected with the spring holder operative to rotate about a longitudinal axis of the mixing chamber wherein the spring is the only means for substantially mixing the liquid component and a powder component within the mixing chamber.

In yet another aspect of the present invention, a device for mixing two components to form a mixture is provided. The device has a mixer section defining a mixing chamber. The device also has a collapsible mixing element holder within the mixing chamber wherein the collapsible mixing element holder defines a passageway between the mixing chamber and the exterior of the mixing chamber. The device also has a collapsible mixing element connected to the collapsible mixing element holder operative to rotate about a longitudinal axis of the mixing chamber. The device also has a drive shaft operative to engage the passageway of the collapsible mixing element holder wherein rotation of the drive shaft causes rotation of the collapsible mixing element holder.

In yet another aspect of the present invention, a method of mixing a first component and a second component in a mixing chamber having a mixing element and dispensing mixed curable material is provided. The method has a step of loading a powder component into the mixing chamber, the mixing chamber having a first end and a second end. The method also has a step of loading a liquid component into the mixing chamber. The method further has the step of inserting a drive shaft into the first end of the mixing chamber. The method also has the step of causing the mixing element to rotate by rotating the drive shaft and mixing the first component with the second component and forming a mixture. The method also has the step of inserting a plunger into the second end of the mixing chamber. The method further has the step of advancing the plunger toward the first end of the mixing chamber, the plunger applying force to the mixture. The method also has the step of dispensing the mixture from the first end of the mixing chamber.

In still another aspect of the present invention, a device for introducing liquid component into a mixing chamber is provided. The device has an elongated ampule holder having a longitudinal axis and having a chamber operative to hold an ampule. The device also has at least one breaker pin slidably received within an opening of the ampule holder wherein rotational movement of the ampule holder causes the at least one breaker pin to move radially inward and pierce an ampule when the ampule is present in the ampule holder.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 5a is a perspective view of a driver connector according to a preferred embodiment of the present invention;

FIG. 5b is a cross-section view of a driver connector according to the preferred embodiment of the present invention depicted in FIG. 5a taken along line 5b-5b of FIG. 5a;

FIG. 6b is a partial cross-section view of an assembled injector according to the preferred embodiment of the present invention depicted in FIG. 6a taken along line 6b-6b of FIG. 6a;

FIG. 8b is a cross-section view of a liquid component delivery system according to the preferred embodiment of the present invention depicted in FIG. 8a taken along line 8b-8b of FIG. 8a;

DETAILED DESCRIPTION OF THE DRAWINGS AND THE PRESENTLY PREFERRED EMBODIMENTS

Figure 1:
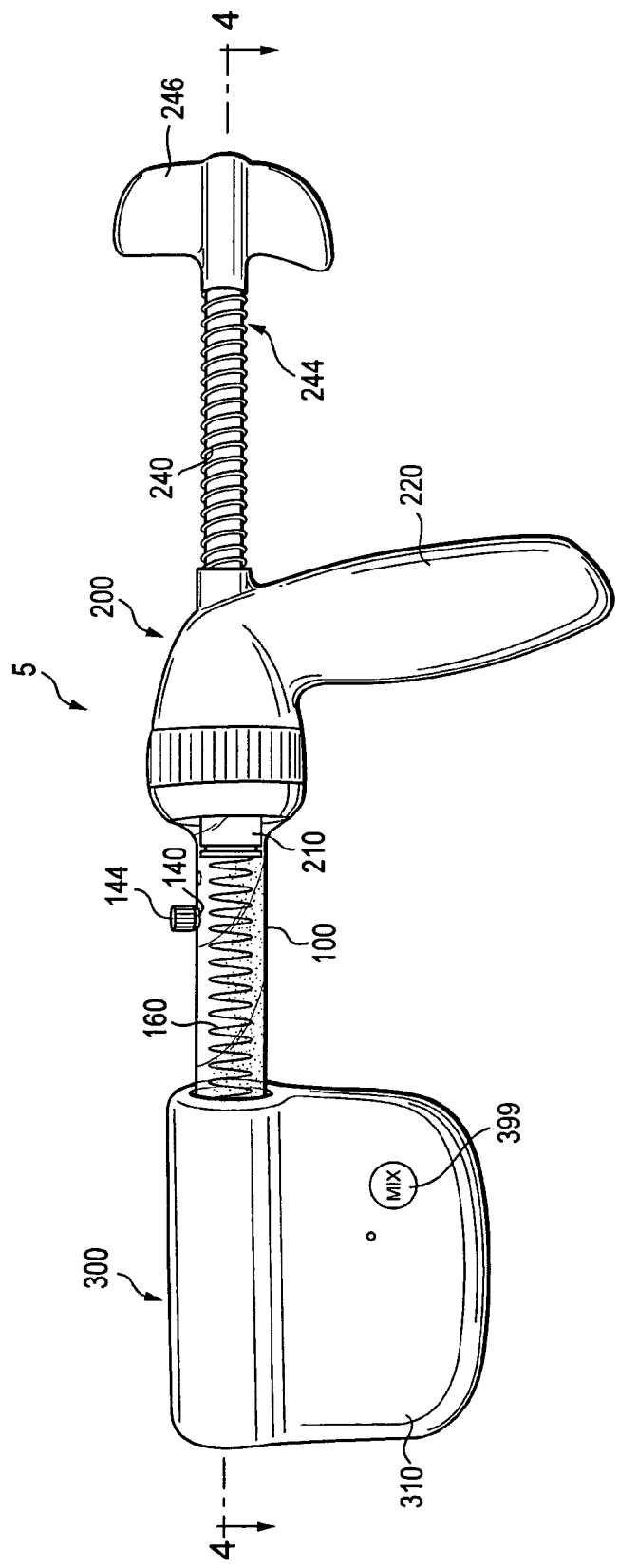
FIG. 1 is a side view of an assembled curable material mixing device according to a preferred embodiment of the present invention.

FIG. 1 illustrates components of a curable material mixing and delivery system 5 according to principles of the present invention. The curable material mixing and delivery system 5 according to a preferred embodiment of the present invention has a mixer section 100 for mixing components of a curable material, an injector 200 for driving curable material out of the mixer section 100 and a driver 300 for mixing the components of the curable material within the mixer section 100. According to one preferred embodiment, and with reference to FIGS. 8-10, the system also includes a liquid component delivery system 400 for delivering a liquid component to the mixer section 100.

Details on the various components are provided below. In general terms, however, two separate components, preferably a liquid component and a powder component, are required to be mixed to form curable material for delivery to a injection site within a patient. With reference to FIG. 1, the mixer section 100 is loaded with a first component, preferably the powder component. The second component, typically a liquid component, is delivered to the mixer section 100 through an introduction port 140 into the mixer section 100. The driver 300 is then activated to rotate a collapsible mixing element 160 within the mixer section 100 to mix the first and second components into the curable material. After mixing, the driver 300 is removed, and a plunger 210 of the injector 200 advances axially within the mixer section 100 to dispense curable material from the mixer section 100 and into a delivery site within a patient. The system 5 can be used for a number of different procedures, including, for example, vertebroplasty and other bone augmentation procedures in which curable material is delivered to a site within bone.

The system 5, and in particular the mixer section 100, is highly useful for mixing a curable material. The phrase "curable material" within the context of the substance that can be delivered by the system/device of the invention described herein is intended to refer to materials (e.g., composites, polymers, and the like) that have a fluid or flowable state or phase and a hardened, solid or cured state or phase. Curable materials include, but are not limited to injectable bone cements (such as PMMA), which have a flowable state wherein they can be delivered (e.g., injected) by a cannula to a site and subsequently cure into hardened curable material. Other materials, such as calcium phosphates, bone in-growth material, antibiotics, proteins, etc., could be used to augment the curable material (but should not affect an overriding characteristic of the resultant formulation having a flowable state and a hardened, solid or cured state).

Figure 2:
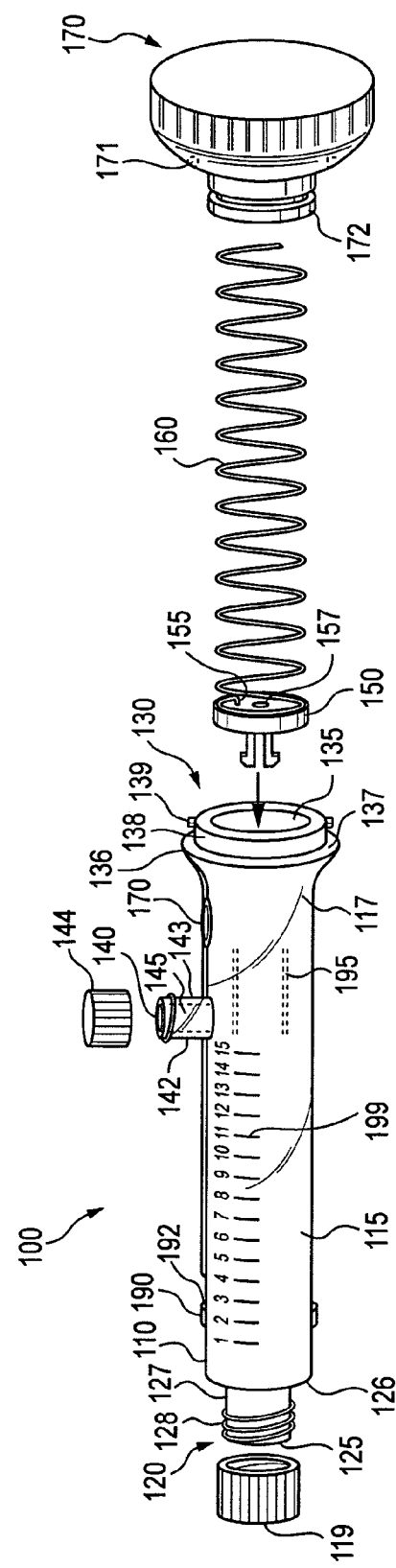
FIG. 2 is an exploded view of the mixer section according to a preferred embodiment of the present invention.

With reference to FIG. 2, a mixer section 100 according to a preferred embodiment is disclosed. The mixer section 100 comprises a housing 110 that defines a mixing chamber 115. The housing 110 further comprises an first end 120 that has an opening 125 to the mixing chamber 115 and a second end 130 that has an opening 135 to the mixing chamber. The housing also contains a port 140 that defines a passageway 145 to the mixing chamber 115.

According to a preferred embodiment depicted in FIG. 2, the housing 110 is generally cylindrical and defines a longitudinal axis. The first end 120 and second end 130 are at opposite ends of the housing with respect to the longitudinal axis. The first end 120 further defines an end shoulder 126 and a cylindrical reduced diameter cylindrical section 127 with respect to the diameter of the mixing chamber 115. According to a preferred embodiment, the reduced diameter cylindrical section 127 also contains threads 128 for mating with corresponding threads on a cap 119 or cannula connector (not shown). The second end 130 preferably defines a substantially conical section 136 having an inner mating surface 137. The second end further defines a cylindrical ring 138 extending axially from the conical section 136. Preferably, the cylindrical ring 138 contains one or more injector locking features 139 that correspond to one or more openings 171 within the collar 170 so that the collar 170 may be removably connected with the housing 110. In this embodiment, after the collar 170 is inserted over the cylindrical ring 138, the collar 170 is rotated slightly to removably lock the collar 170 to the housing 110. As will be described in detail below, the injector locking features 139 also correspond to openings in the injector 200 to removably attach the housing to the injector 200. Preferably, the injector locking features 139 and corresponding openings 171 are keyed so that the collar 170 can be attached to the housing 110 in one preferred orientation. Although this embodiment uses injector locking features 139 to connect the housing 110 with the collar 170, one skilled in the art would know that other attachment means, such as a threaded connect or press-fit connection, may also be used.

Figure 4:
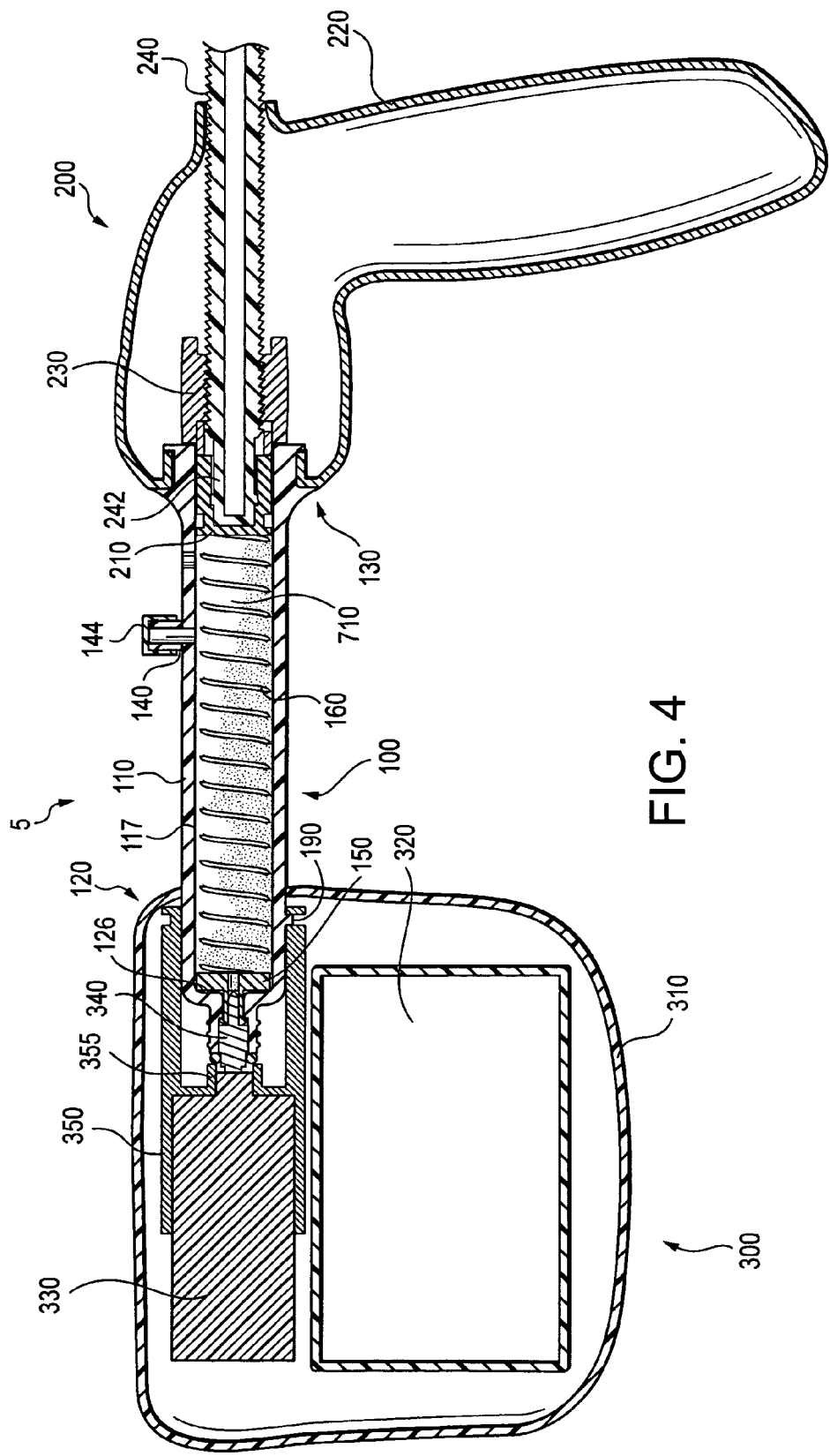
FIG. 4 is a partial cross-section view of an assembled curable material mixing device according to a preferred embodiment of the present invention taken along line 4-4 of FIG. 1.

A port 140 is located at a radial outer surface of the housing 110. The port 140 preferably contains a cylindrical projection 142 and defines a passageway 145 to the mixing chamber 115. The port may also contain threading 143 so that the port may connect with a cap 144 or other device having corresponding threading. The port 140 is preferably located proximal to the second end 130 of the housing 110. Pressure within the mixing chamber 115 can become significant when the curable material is being dispensed from the mixing chamber 115. As will be explained in more detail below, the plunger 210, as depicted in FIG. 4, of the injector 200 will advance axially within the mixing chamber 115 to dispense the curable material. Large pressures within the mixing chamber 115 are not generally created until the plunger 210 has moved axially within the mixing chamber 115 toward the first end 120 of the housing 110 and until the curable material is substantially compacted within the first end 120 of the housing 110. In order to avoid dispensing material through the port 140, the port 140 is preferably located at a position toward the second end 130 of the housing 110. In this way, the plunger 210 will preferably pass beyond the location of the port 140 before the formation of significant pressure within the mixing chamber 115.

With reference to FIG. 2, the housing also contains one or more vents 170 for releasing gas from within the mixing chamber 115. Preferably, the one or more vents 170 are located on the radial outer surface of the housing 110. The vents 170 are preferably covered with a filter material so that gas escaping from the mixing chamber 115 has a reduced odor that is associated with the curable material. Preferably, the filter material is a Gore-tex® covering. Other filtering material, such as charcoal filtering material, may also be used. In order to avoid dispensing curable material through the one or more vents 170, the one or more vents 170 are preferably located at a position toward the second end 130 of the housing 110. In this way, the plunger 210 will preferably pass beyond the location of the one or more vents 170 before the formation of significant pressure within the mixing chamber 115.

With reference to FIG. 2, according to one preferred embodiment, the housing 110 also contains one or more driver locking features 190 to aid in removably connecting the housing 110 with the driver 300. Preferably, the driver locking features 190 are located on the radial outer surface of the housing 110. In this embodiment, the driver locking features project 190 radially from the housing and define one or more faces 192 perpendicular to the longitudinal axis of the mixing chamber. As will be described in more detail below, the projections 190 correspond to openings 360 in the driver connector 350 of the driver, as depicted in FIG. 5b. Preferably, the driver locking features 190 and corresponding driver connector openings are keyed so that the driver 300 can be attached to the housing 110 in one preferred orientation. Although this embodiment uses locking projections 190 to connect the housing with the driver 300, one skilled in the art would know that other attachment means, such as a threaded connect or press-fit connection, may also be used.

With reference to FIG. 2, the inner surface 117 of the housing 110 also defines one or more shallow grooves 195. The one or more grooves 195 are preferably located proximal to the second end 130 of the housing and are operative to allow air or other gas to travel around the plunger 210 as the plunger 210 advances axially through the mixing chamber 115.

The housing 110 is preferably transparent to provide the physician the ability to see the contents of the mixing chamber 115. This will allow the physician to see the progress of the mixing step of the components and to visually inspect the consistency of the curable material. The housing is preferably made of cyclic olefin copolymer (COC), but may also be made of nylon, polycarbonate, Lexan®, and any other transparent material suitable for use with curable material, suitable for use at significant pressure, and suitable to withstand sterilization. With continued reference to FIG. 2, the housing 110 preferably also contains visual indicia 199 to indicate the volume of the curable material within the mixing chamber 115. The visual indicia 199 may be molded onto the housing 110, or may painted or otherwise printed on the housing 110.

Figure 3B:
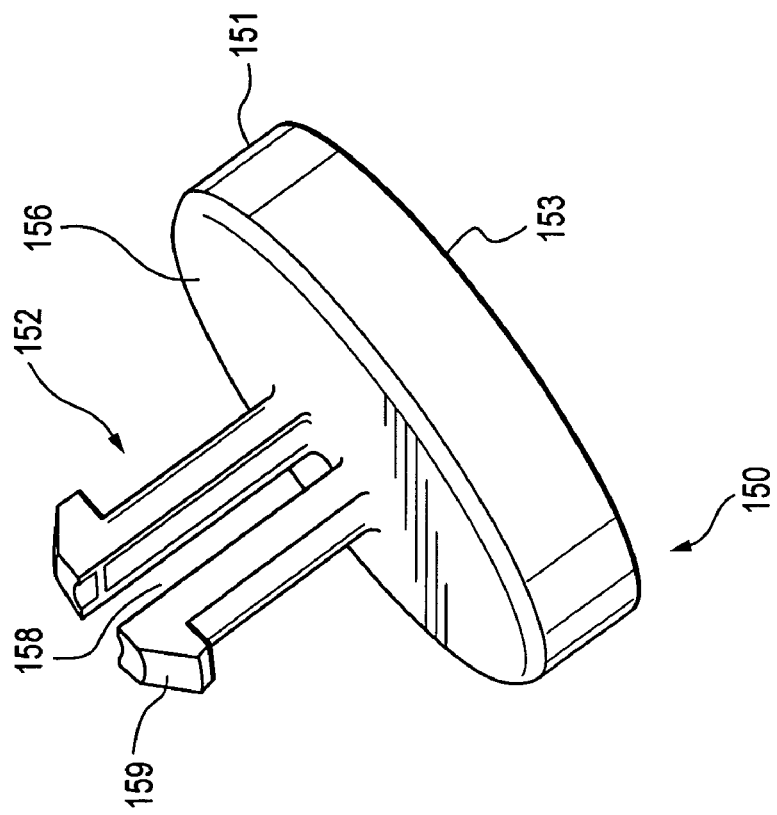
FIGS. 3a and 3b are perspective views of a mixing element holder according to a preferred embodiment of the present invention.
Figure 3A:
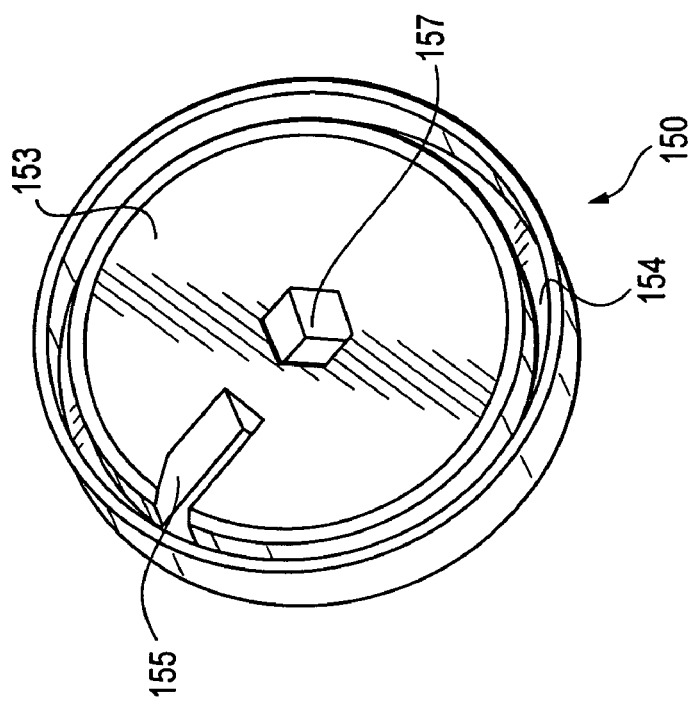

The mixer section 100 also has mixing element holder 150 and a collapsible mixing element 160 for mixing the components of the curable material. The mixing element holder 150 connects to the collapsible mixing element 160 and both are located at least partially within the mixing chamber 115. With reference to FIGS. 3a and 3b, according to a preferred embodiment, the mixing element holder 150 contains a disk-shaped portion 151 and a reduced diameter slotted projection 152. A first end 153 of the mixing element holder contains a collapsible mixing element retaining ring 154 for fixedly retaining the collapsible mixing element 160. In one embodiment, the mixing element holder 150 contains a retaining slot 155 that is perpendicular to the longitudinal axis of the mixing chamber 115. This slot 155 retains a perpendicular projection of the collapsible mixing element 160 as to fixedly retain the collapsible mixing element 160 from moving rotationally with respect to the mixing element holder 150. With continued reference to FIG. 3b, and reference to FIG. 4, a second surface 156 of the mixing element holder 150 engages the inner surface of the shoulder 126 of the first end 120 of the housing 110. The mixing element holder 150 further defines a passageway 157 that is operative to allow curable material to flow from within the mixing chamber 115 to outside the mixing chamber 115. The slotted projection 152 of the mixing element holder 150 preferably extends within the reduced diameter cylindrical section 127 of the first end 120 of the housing 110. According to a preferred embodiment, the slotted projection 152 comprises two projections separated by a slot 158 that is coaxial with the passageway.

With reference to FIGS. 3b and 4, the slotted projection 152 and passageway 157 are operative to removably engage a drive shaft 340 of the driver 300. The drive shaft 340 and the mixing element holder 150 interact so that rotation of the drive shaft 340 rotates the mixing element holder 150 and thus, the collapsible mixing element 160. In the preferred embodiment depicted in FIGS. 3a and 3b the slotted projections 152 and the passageway 157 of the mixing element holder 150 form hexagonal surfaces that are operative to engage a hexagonal drive shaft 340. In another embodiment, the drive shaft may be similar in shape to a flat-ended screw driver and the mixing element holder may define a corresponding slot. One skilled in the art will know other suitable configurations to allow the drive shaft 340 to rotationally drive the mixing element holder 150 in a removable manner.

With reference to FIGS. 3b and 4, in one preferred embodiment the slotted projection 152 contains one or more fingers 159 that extend perpendicularly to the longitudinal axis of the mixing chamber 115. The one or more fingers mate with corresponding surfaces in the reduced diameter cylindrical section 127 of the housing 110 that are also perpendicular to the longitudinal axis of the mixing chamber. In this embodiment, the mixing element holder 150 is substantially retained from moving axially within the mixing chamber 115. In the embodiment where the projections are separated by a slot 158, one skilled in the art will understand that when the mixing element holder 150 is placed within the mixing chamber 115, the slot 158 between the projections 152 allow the projections to bend toward each other so that the fingers 159 may be inserted through the reduced diameter section 127 at the first end 120 of the housing 110. The reduced diameter section 127 is adapted so that when the mixing element holder 150 is fully inserted into the housing 110, the projections 152 snap outward and the fingers 159 engage the corresponding surfaces of the housing 110 that are perpendicular to the longitudinal axis of the mixing chamber 115.

With reference to FIG. 4, according to one preferred embodiment, the collapsible mixing 160 element extends substantially the entire length of the mixing chamber 115. As will be described in more detail below, the collapsible mixing element 160 mixes the components of the curable material when the collapsible mixing element 160 is rotated about the longitudinal axis of the mixing chamber 115. The collapsible mixing element 160 is also operative to collapse within the mixing chamber 115 as the plunger 210 is moved axially within the chamber 115.

According to the preferred embodiment of FIG. 2, the collapsible element is a spring-like element having a wire diameter from approximately 0.010 inches to approximately 0.050 inches (approximately 0.254 mm to approximately 1.27 mm) and more preferably, approximately 0.024 inches (approximately 0.61 mm). The collapsible mixing element 160 is also preferably made of stainless steel. In this embodiment, the diameter of the collapsible mixing element 160 is preferably slightly less than the diameter of the mixing chamber 115 to prevent the collapsible mixing element 160 from locking against the inner surface 117 of the housing 110. A radial clearance of zero inches to approximately 0.5 inches (approximately 12.7 mm) may be used, and more preferably a clearance of approximately 0.045 inches (approximately 1.14 mm) is used. Additionally, according to one preferred embodiment, the outer diameter of the spring should be approximately 0.578 inches (approximately 14.68 mm) to approximately 0.618 inches (approximately 15.70 mm), and is more preferably 0.598 inches (approximately 15.19 mm). Non-spring-like collapsible mixing elements may also be used. In one preferred embodiment, the collapsible mixing element is one or more loops extending within the mixing chamber. In an embodiment having two or more loops, the collapsible mixing element forms a whisk-like configuration. In another preferred embodiment, the collapsible mixing element is a single somewhat flexible, substantially straight element, such as a wire, that may be connected to the mixing element holder off-center of the holder. In this embodiment, rotation of the mixing element holder causes the element to rotate and whip within the chamber. In another preferred embodiment, the collapsible mixing element is two or more somewhat flexible, substantially straight elements, such as wires, wherein rotation of the mixing element holder causes the elements to rotate and whip within the chamber. In another preferred embodiment, the collapsible mixing element is at least one curved element extending substantially the entire length of the mixing chamber. The above mixing element embodiments are operative to bend and otherwise collapse within the mixing chamber when engaged by an advancing plunger. One skilled in the art will understand that each of these embodiments can be used alone, in combination with a spring-like element, or in combination with each other.

According to a preferred embodiment depicted in FIG. 2, the mixer section 100 also comprises a removable collar 170 connected to the housing 110. In this embodiment, the collar 170 is removably connected with the second end of the housing 110 and acts as cap on the housing 110 for transportation and storage. The collar contains a stopper 172 operative to seal the second end of the housing 110. The stopper 172 preferably is substantially the same diameter of the mixing chamber and forms a seal so that component material does not escape around the stopper 172.

The mixing section also comprises a removable cap 119 that may be attached to the reduced diameter section 127 of the housing 110 during transportation and storage. The cap 119 is removed prior to use to allow the driver 300 to be attached to the housing 110.

With reference to FIG. 4, the curable material mixing and delivery system 5 also comprises a removable driver 300. The driver 300 provides the force to rotate the collapsible mixing element 160 to mix the components of the curable material. In a preferred embodiment according to FIG. 4, the driver 300 comprises a shell 310 for conveniently manipulating the driver 300. The driver 300 further comprises a battery 320, a motor 330 and drive shaft 340 within the shell 310. The driver 300 also comprises a driver connector 350 for connecting the mixer device 100 with the driver 300. Preferably, the driver connector 350 is located at an opening on the shell 310 and is operative to receive an end of the mixer section 100. In one preferred embodiment depicted in FIGS. 5a and 5b, the driver connector 350 provides a support for the motor 330 and the drive shaft 340 and provides the corresponding openings 360 for receiving the driver locking features 190 of the housing 110. In this embodiment, the motor 330 is located in an opening 370 at a first end 372 of the driver connector 350. A drive shaft 340 is connected to the motor 330 and extends through a divider 355 and into an 380 opening at the second end 382 of the driver connector 350. An O-ring 390 is preferably located at the intersection of the drive shaft 340 and divider 355 to prevent gas or curable material to escape from the mixer device 100 when the mixer section 100 is connected with the driver 300. The driver connector 350 further defines one or more grooves 365 for receiving the driver locking features 190 of the housing 110, and thus removably connecting the driver connector 350 with the housing 110. The driver locking features 190 of the housing 110 are operative to be inserted into the one or more openings 360 and grooves 365 of the driver connector 350 and rotated to removably lock the mixer section 100 with the driver 300. Preferably, the driver locking features 190 and corresponding driver connector openings 360 and grooves 365 are keyed so that the driver can be attached to the mixer device in one preferred orientation.

With reference to FIG. 4, the drive shaft 340 is operative to rotate the mixing element holder 150 of the mixer section 100. In a preferred embodiment, the drive shaft 340 is hexagonal and the slotted projections 152 and the passageway 157 of the mixing element holder 150 form corresponding female hexagonal surfaces. In another embodiment, the drive shaft may be similar in shape to a flat-ended screw driver and the mixing element holder defines a corresponding slot. One skilled in the art will know other suitable configurations to allow the drive shaft to rotationally drive the mixing element holder.

The driver motor 330 may be activated in various ways. According to one preferred embodiment, a button 399, depicted in FIG. 1, is located at an opening in the shell 310 to activate the motor 330 when depressed.

With reference to FIGS. 1 and 4, the curable material mixing and delivery system 5 also comprises an injector 200. The injector provides the force to advance the plunger 210 axially within the mixer section 100 and deliver curable material to a delivery site. According to one preferred embodiment, the injector 200 comprises a grip section 220 to allow a physician to conveniently manipulate the injector 200. In this embodiment, the injector 200 further comprises an internal threaded portion 230 and a threaded rod 240. The threaded rod 240 contains a first end 242 proximal to the plunger 210. The threaded rod also contains a second end 244 distal from the plunger and having a handle 246. The threaded rod 240 and internal threaded section 230 are operative so that when the handle 246 is turned, the threaded rod 240 moves axially in the direction of the first end 120 of the mixer section 100. As the threaded rod 240 moves axially, it advances the plunger 210 axially within the mixing chamber 115.

The injector further comprises an interface to connect to the second end 130 of the housing 110 in a fashion similar to the manner the first end 120 of the housing 110 removable connected to the driver 300. In one embodiment, one or more injector locking features 139 of the second end 130 of the housing 110 correspond to openings and grooves in the injector 200 to removably connect the injector 200 with the housing 110. The injector locking features 139 of the housing 110 are operative to be inserted into the one or more openings of the injector 200 and rotated within a groove to removably lock the mixer section 100 with the injector 200. Preferably, the injector locking features 139 and corresponding openings and grooves of the injector 200 are keyed so that the injector can be attached to the housing 110 in one preferred orientation. Although this embodiment uses injector locking features 139 to connect the housing 110 with the injector 200, one skilled in the art will understand that other attachment means, such as a threaded connect or press-fit connection, may also be used.

Figure 6A:
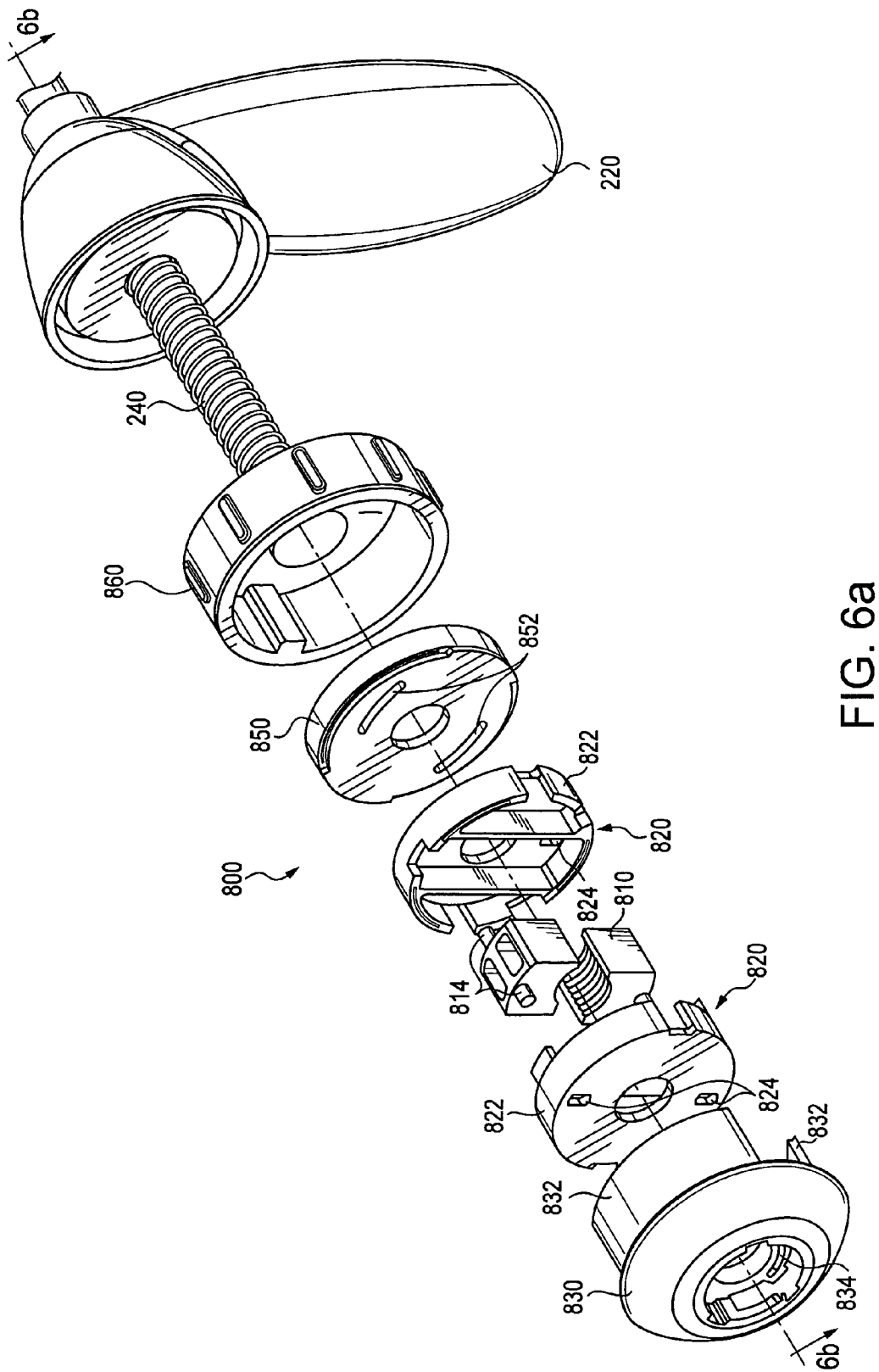
FIG. 6a is a partial exploded view of an injector according to a preferred embodiment of the present invention.
Figure 6B:
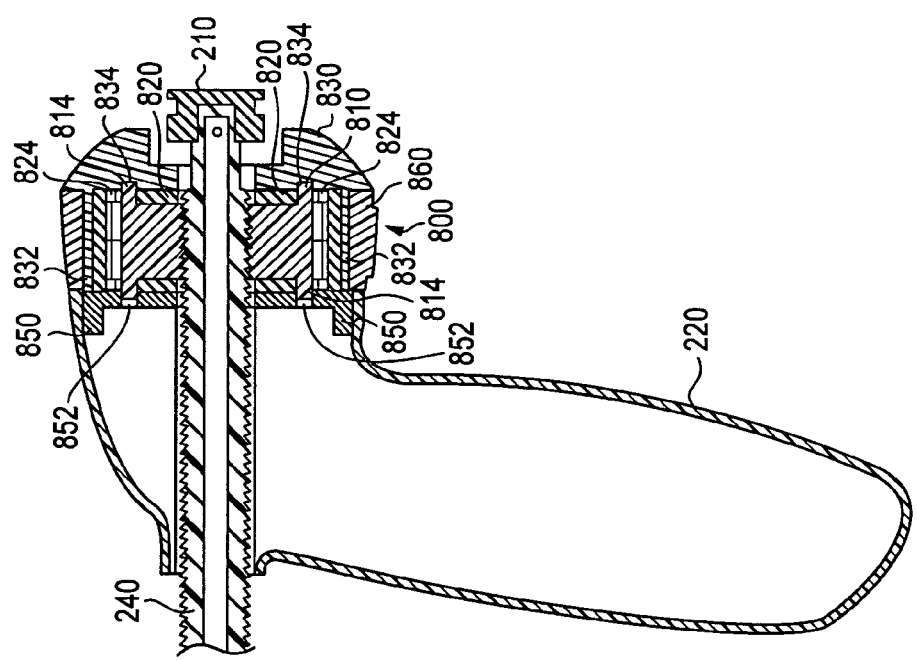

According to one preferred embodiment depicted is FIGS. 6a and 6b, the injector 200 further comprises a release 800 to allow the threaded rod 240 to be indexed axially quickly without requiring the rod 240 to be rotated. In this embodiment, internal threaded section 810 are operative to disengage from the threaded rod 240 to allow the rod 240 to slide freely axially. According to one preferred embodiment of the injector 200 depicted in FIGS. 6a and 6b, the injector release 800 comprises two internal threaded sections 810 that are operative to engage the threaded rod 240. Each internal threaded section contains two posts 814. The threaded sections 810 are contained within a rotatable container 820. The rotatable container 820 is comprised of two container halves 822. Each container half 822 contains two radially oriented slots 824 operative to receive the posts 814 of the internal threaded sections 810 when the container halves 822 are connected together. In this embodiment, the internal threaded sections 810 are slidable within the rotatable container 820. The posts 814 of the internal threaded sections 810 extend to outside of rotatable container 820. The injector release 800 also comprises a shoulder 830 having two guide fins 832 and a first pair of transverse slots 834. The guide fins 832 are operative to hold the rotatable container 820, but allow rotation of the rotatable container 820 therein. A post 814 of internal threaded section 810 extends through the transverse slots 834 of the shoulder 830. The injector release 800 also comprises a threaded rod guide 850. The threaded rod guide 850 defines a center opening operative to receive and support the threaded rod 240 and defines a second pair of transverse slots 852. The threaded rod guide 850 is operative to fit within the guide fins 832 of the shoulder 830. A post 814 of each internal threaded section 810 extends through the transverse slots 852 of the threaded rod guide 850. An injector collar 860 fits over the guide fins 832 of the shoulder 830 and is operative to rotate around the guide fins 832 of the shoulder 830. The injector collar 860 also engages the rotatable container 820 such that rotation of the injector collar 860 rotates the rotatable container 820 within the guide fins 832. Rotation of the rotatable container 820 causes the posts 814 to slide translationally within the transverse slots 834, 852. Because the posts 814 are also constrained by the radial slots 824 of the rotatable container 820, translational movement causes the internal threaded sections 810 to move radially within rotatable container 820. Rotation of the injector collar 860 thus causes the internal threaded sections 810 to radially move in or out from the threaded rod 240. When the internal threaded sections 810 are positioned radially outward from the threaded rod 240, the threaded rod 240 is disengaged from the internal threaded sections 810 and can freely move axially. When the internal threaded sections 810 are position radially inward from the threaded rod 240, the threaded rod 240 is engaged with the internal threaded sections 810 and must be turned to move axially.

In operation of the device according to the present invention, the curable material delivery system 5 is preferably prepackaged in a kit. In a first step the mixer section 100, driver 300 and injector 200 are assembled to form the curable material delivery device 5. According to one preferred embodiment, the mixer section 100 is prepackaged with a predetermined volume of powder component. In another embodiment the removable cap 119, removable collar 170 or removable port cap 144 may be removed from the housing 110 to allow powder component to be introduced into the mixing chamber 115. It is understood by one skilled in the art that the powder component may be comprised of additives additional to powder polymer. The additives include other materials, such as calcium phosphates, bone in-growth material, antibiotics, and proteins.

In a preferred embodiment where the powder component had been preloaded into the mixing chamber 115, the removable cap 119 is removed and the driver 300 is connected to the first end 120 of the housing 110. When connecting the driver 300 to the housing, the drive shaft 340 of the housing must be inserted into the passageway 157 of the mixing element holder 150 so that the drive shaft 340 engages and rotates the mixing element holder 150 when the drive shaft 340 is rotated. The removable collar 170 is also removed and the injector 200 is connected to the second end 130 of the housing 110. It is understood that care should be taken avoid spilling the powder component contents from the housing when the cap or collar are removed from the housing. When connecting the injector 200 to the housing 110, the plunger 210 should be in a retracted position so that the liquid component can be introduced into the mixing chamber 115 through the port 140.

After the driver 300 and injector 200 are connected to the housing 110, the port cap 144 is removed from the port 140 and the liquid component is introduced into the mixing chamber 115. Devices for introducing liquid component into the mixing chamber are described in detail below. According to one embodiment, the port cap 144 is then placed back onto the port 144. After introduction of the liquid component the curable material components are ready to be mixed. Preferably, the physician activates the motor 330 of the driver 300, causing the drive shaft 340 to rotate rapidly. Rotation of the drive shaft 340 causes the mixing element holder 150 and the collapsible mixing element 160 to also rotate rapidly. The components are mixed until the mixture contains the optimum properties for the desired application. For an embodiment using PMMA loaded with barium sulphate, the components are preferably mixed between approximately 30 and approximately 150 seconds and are more preferably mixed for approximately 90 seconds. According to one preferred embodiment, the driver 300 is pre-programmed to cycle through a predetermined mixing sequence. In this embodiment, the physician need only press the mix button 399 and the driver 300 will automatically mix the materials according to a predetermined length of time, speed and rotational direction to obtain the optimum properties of the curable material. According to one preferred embodiment, the mixing element 160 is rotated by the driver 300 in a first direction for a predetermined period of time, and then rotated in the opposite direction for a predetermined period of time. In another preferred embodiment, rotational direction alternates during the mixing cycle.

After the components are mixed the driver 300 is removed from the first end 120 of the housing 110. According to one preferred embodiment depicted in FIG. 7, the first end 120 of the housing 110 is then connected to a cannula 700 for delivery of curable material to a delivery site within a patient.

With reference to FIG. 4, after the driver is removed, the plunger 210 is advanced axially within the chamber 115 toward the first end 120. According to a preferred embodiment, the mixed curable material does not occupy the entire volume of the mixing chamber 115. As a result, gas pockets 710 exist within the mixing chamber 115. As the plunger 210 is advanced within the mixing chamber 115 toward the first end 120 of the housing 110, gas is allowed to escape through one or more grooves 195 on the inner surface of the housing 110 toward the second end 130 of the housing 110 and rearward of the plunger 210. The grooves 195 advantageously allows gas to be removed from the curable material as the plunger 210 advances and compresses the curable material. The removal of gas from the curable material beneficially provides a more consistent curable material and more efficient delivery of curable material. According to another preferred embodiment, gas is also allowed to escape from the mixing chamber 115 through filtered vents 170 on the housing. It will be appreciated by one skilled in the art that the injector plunger 210 may be more easily advanced when the curable material contains gas pockets 710 and is thus less dense. As the gas is removed from the curable material, the curable material becomes more dense and greater force is required to advance the plunger 210. According to one preferred embodiment described above, the threaded rod 240 may be released from the internal threaded sections 230 of the injector 200. In this embodiment the plunger 210 may be quickly pushed toward the first end 120 of the housing 110 to compress the curable material and remove gas from the curable material. When high resistance from dense curable material is experienced, the internal threaded section 230 can be caused to engage the threaded rod 240, and the plunger 210 can be further advanced by rotating the handle 246 on the threaded rod 240.

Figure 7:
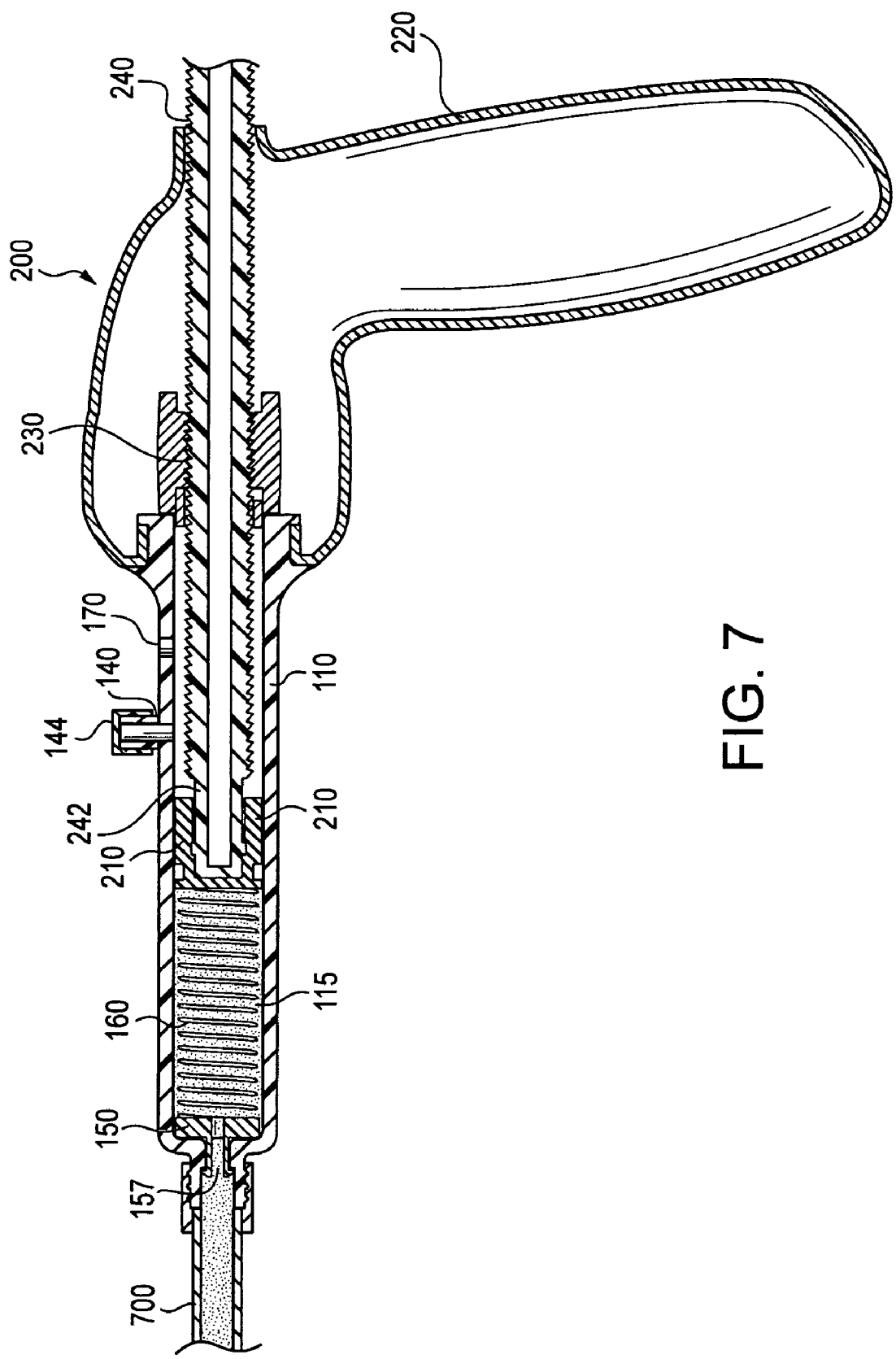
FIG. 7 is a partial cross-section view of a curable material mixing device according to a preferred embodiment of the present invention during delivery of the mixed curable materials.

With reference to FIG. 7, as the plunger 210 is indexed toward the first end 120 of the housing 110, the plunger 210 engages the collapsible mixing element 160 and causes the collapsible mixing element 160 to collapse within the first end 120 of the housing 110. Additionally, as the plunger 210 is indexed toward the first end 120 of the housing 110, curable material is forced through the passageway 157 in the mixing element holder 150 and curable material is thus dispensed from the first end 120 of the housing 110.

Various manners can be utilized to deliver the liquid component for mixing with a powder component. According to one prior art method, an ampule 410 (by way of example, see FIG. 8a) filled with liquid component can be broken to deliver the liquid component. The ampule is typically made of a brittle casing, such as glass, that can be broken to release the liquid component. An ampule 410 typically comprises a body 412, a neck 414, and a tip 416. In this method, the neck 414 is typically scored to allow a physician to break the tip 416 from the body 412 by hand. The contents of the body 412 may then be emptied into a mixing bowl. In this prior art method, however, the ampule 410 may crumble in the physician's hands, exposing the physician to sharp objects, obnoxious fumes, and causing the liquid contents to be spilled.

Figure 8A:
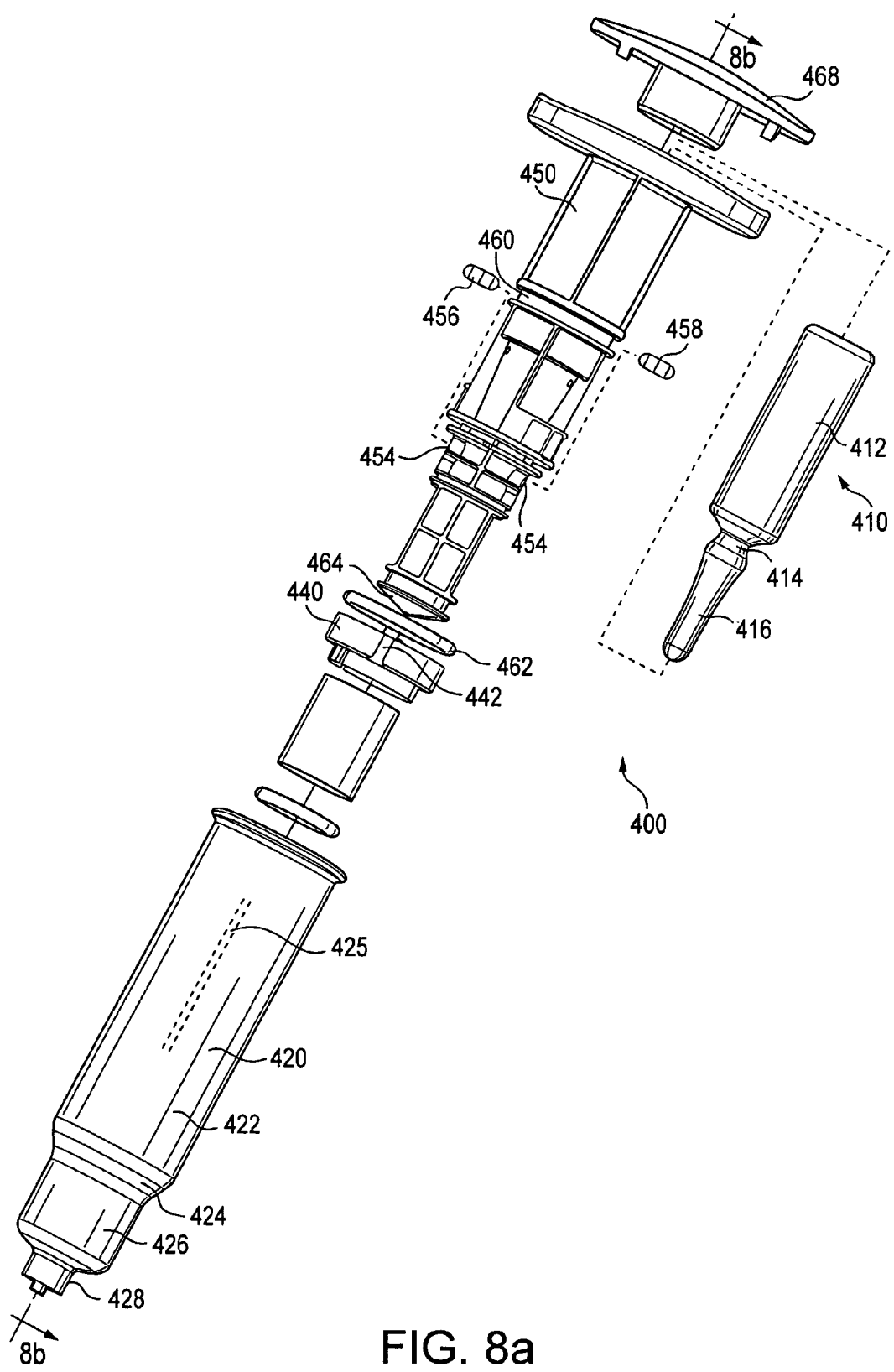
FIG. 8a is a perspective view of a liquid component delivery system according to a preferred embodiment of the present invention.
Figure 8B:
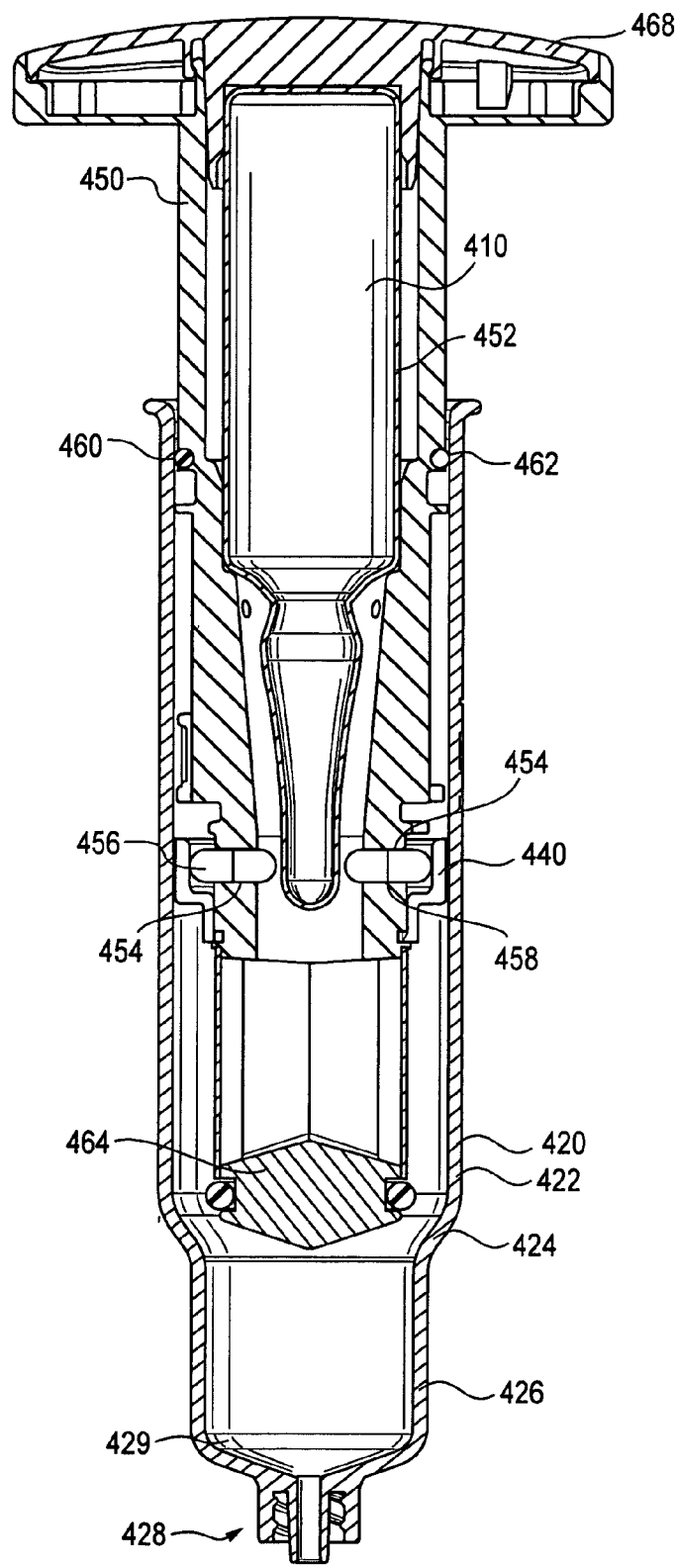

According to one preferred embodiment of the present invention, and with reference to FIGS. 8a and 8b, the curable material mixing and delivery system 5 also comprises a liquid component delivery system 400 for delivering a liquid component to the mixing chamber 115. In the embodiment depicted in FIGS. 8a and 8b, an ampule 410 is placed inside of a syringe-like assembly wherein the ampule 410 can be broken and the liquid component delivered to the mixing chamber 115 in a closed system. The physician is thus not required to handle the ampule to break it and is not exposed to the fumes and odor associated with the liquid component. The liquid component delivery system 400 according to the preferred embodiment of FIGS. 8a and 8b comprises a syringe barrel 420, a cam 440 and a liquid component plunger 450. The syringe barrel 420 is preferably cylindrical and comprises a larger diameter section 422 and a reduced diameter section 426 connected by a transition section 424. The inner surface of the syringe barrel 420 defines one or more guide ridges 425 protruding from the inner surface of the syringe barrel and extending longitudinally along a section of the barrel 420. The syringe barrel 420 is preferably transparent to provide the physician with a visual indication of the location of the liquid component plunger 450 and the contents of the ampule 410. The syringe barrel 420 is preferably made of polyethylene. According to one preferred embodiment, the reduced diameter section has a filter 429 to filter glass particles from the broken ampule but allow the liquid component to pass therethrough.

The liquid component plunger 450 is operative to being inserted into the syringe barrel 420. The liquid component plunger 450 contains an inner ampule compartment 452 for holding an ampule 410. The liquid component plunger 450 also contains one or more openings 454 operative to slidably hold one or more breaker pins 456. Each breaker pin preferably contains one or more o-rings 458 to prevent liquid component from flowing around the breaker pins 456. The liquid component further comprises a groove 460 to accommodate an o-ring 462. The o-ring 462 prevents fumes and odors associated with the liquid component from escaping the system. The liquid component plunger 450 also comprises a plunger tip 464 proximal to the output end 428 of the syringe barrel 420. The plunger tip 464 is preferably cylindrical and is substantially the same diameter of reduced diameter section 426 of the syringe barrel 420 so that the tip 464 is capable of creating a seal between the tip 464 and the reduced diameter section 426 of the syringe barrel 420. The plunger tip 464 is preferably made of a flexible material and is preferably press fit onto the end of the liquid component plunger 450. The liquid component plunger 450 also contains a removable cap 468 that is placed over the ampule compartment 452 to hold the ampule 410 in place and further provide a seal for fumes or odors. The liquid component plunger 450 also comprises the cam 440. The cam 440 is attached to the liquid component plunger 450 proximal to the breaker pin openings 454 and is operative to allow the liquid component plunger 450 to rotate relative to the cam 440.

Figure 9A:
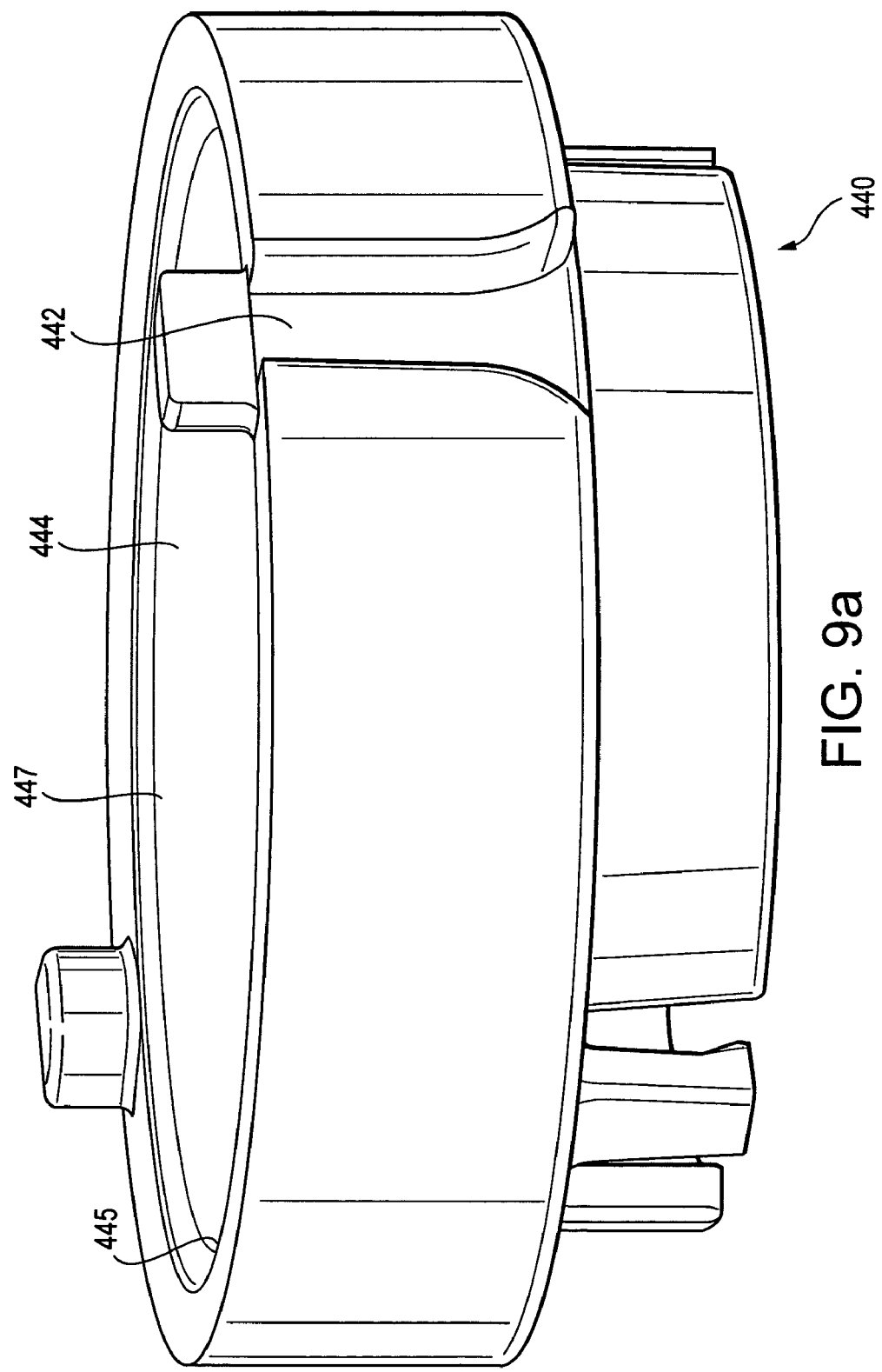
FIGS. 9a and 9b are perspective views of a cam according to a preferred embodiment of the present invention.
Figure 9B:
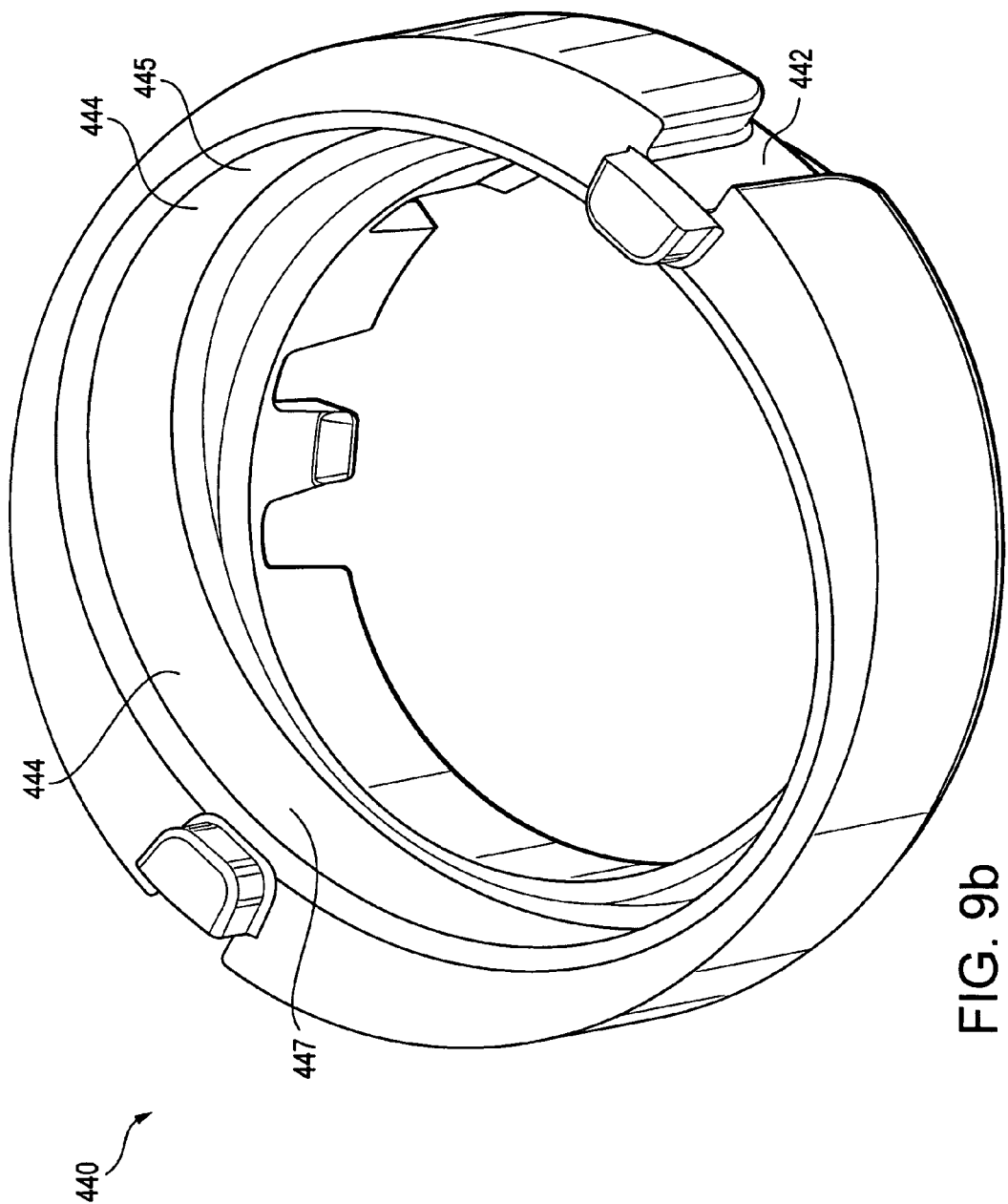

With reference to FIGS. 9a and 9b, the cam 440 is generally cylindrical and contains at its center an opening to allow the liquid component plunger 450 to pass there through. One or more guide ridges 425 of the syringe barrel 420 engage one or more interface grooves 442 on the cam. The cam 440 is positioned within the syringe barrel 420 such that the guide ridges prevent the cam 440 from rotating within the syringe barrel 420. Inner cam surfaces 444 of the cam 440 define a generally oval shape. The generally oval shape of the cam surfaces 444 allow the ampule breaker pins 456 to extend outside of the liquid component plunger 450 when the liquid component plunger 450 is in a first orientation. When the liquid component plunger 450 is rotated 90 degrees to a second orientation, the breaker pins 456 slide along the cam surfaces 444 from the wide inner section 445 of the cam 440 to the narrow inner section 447 and thus drive the breaker pins 456 toward the center of the liquid component plunger 450.

In operation of the liquid component delivery system 400, the liquid component plunger 450 and cam 440 are positioned within the syringe barrel 420. The liquid component plunger 450 is preferably position axially within the syringe barrel 420 so that the plunger tip 464 is within the larger diameter section 422 of the syringe barrel 420 and just above the transition region 424. The liquid component plunger 450 is in the first orientation to allow the breaker pins 456 to extend outside of the liquid component plunger 450 and into the wider inner section 445 of the cam 440. An ampule 410 is placed inside of the ampule compartment 462. When the liquid component plunger 450 is in the first orientation the tip of the ampule 410 is located between the breaker pins 456. The cap 468 is then placed onto the liquid component plunger 450.

According to one preferred embodiment, the liquid component delivery system 400 is then attached to the mixer section 100. Preferably, the liquid component delivery system 400 is oriented vertically above the mixer section 100 to allow liquid component to flow by gravity into the mixer section 100 after the ampule 410 is broken. After attachment to the mixer section 100, the liquid component plunger 450 is rotated 90 degrees relative to the syringe barrel 420. As the liquid component plunger 450 is rotated 90 degrees, the breaker pins 456 slide along the cam surfaces 444 and are forced inward. The breaker pins 456 thus move toward the center of the liquid component plunger 450 as the breaker pins 456 travel from the wider inner section 445 of the cam 440 to the narrow inner section 447 of the cam 440. The inward motion of the breaker pins 456 cause the tips of the breaker pins 456 to penetrate the tip 416 of the ampule 410 and release the liquid component.

By gravity, the liquid component flows into the reduced diameter section 426 of the syringe barrel 420. The liquid component plunger 450 is then axially pushed so that the plunger tip 464 engages the inner surface of the reduced diameter section 426 of the syringe barrel 420. Continued downward motion creates pressure in the syringe barrel 420 that further assists in forcing the liquid component into the mixer section 100.

Figure 10:
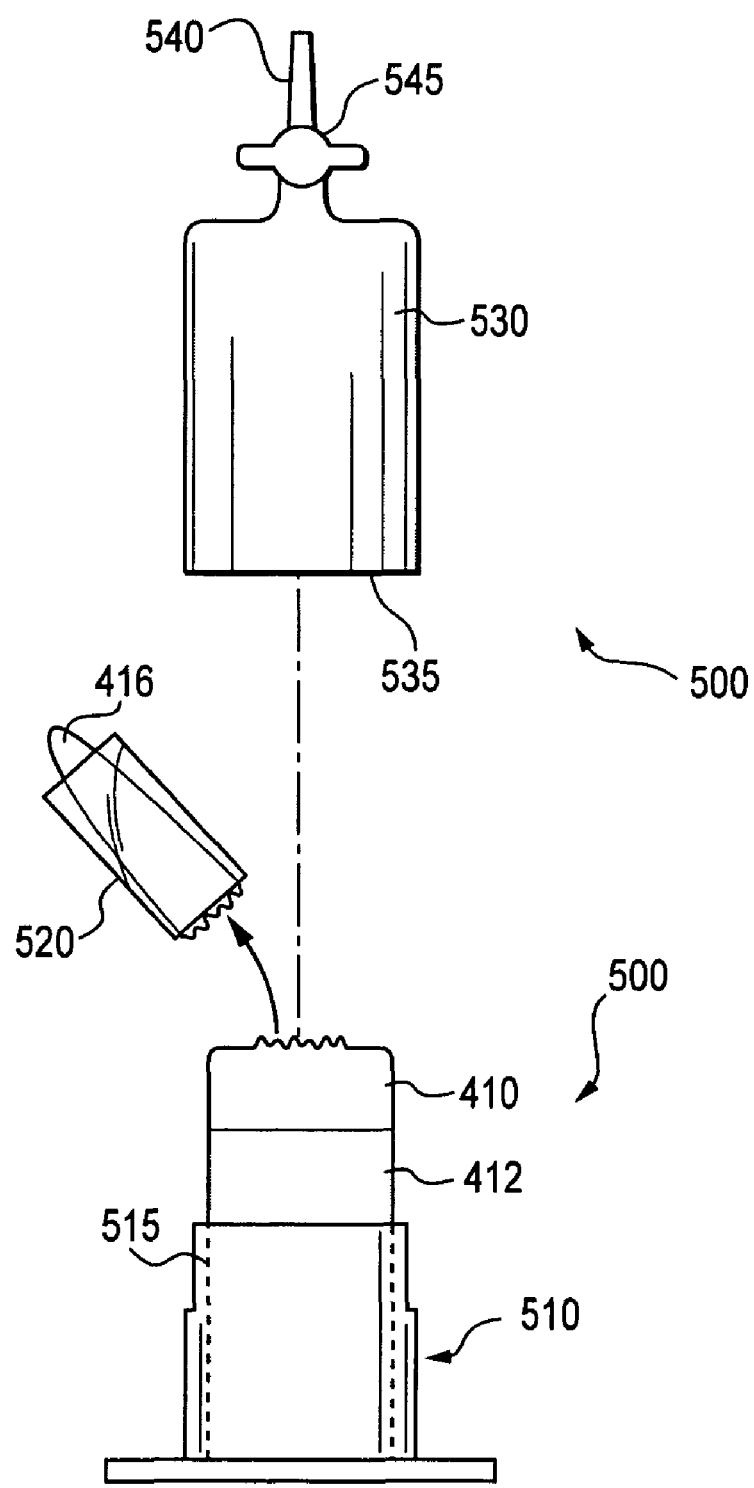
FIG. 10 is an exploded view of a liquid component delivery system according to a preferred embodiment of the present invention.

According to another preferred embodiment of the present invention, and with reference to FIG. 10, the curable material mixing and delivery system 5 comprises a liquid component delivery system 500 for delivering a liquid component to the mixing chamber 115. In this embodiment, an ampule is broken by hand, however, protections are provided to the physician. The liquid component delivery system 500 comprises a base 510, a protective sleeve 520 and a cap 530. The base 510 is preferably cylindrical and defines a chamber 515 operative to hold the body 412 of an ampule 410. The protective sleeve 520 is operative to fit over the tip 416 of an ampule 410. The protective sleeve 520 is preferably made of a durable material capable of resisting puncture by sharp objects. The cap 530 is preferably cylindrical and defines a chamber 535 operative to hold the body 412 of an ampule 410. The cap 530 also contains a needle section 540. The needle section 540 is operative to engage a port 140 on a mixing chamber 115 to deliver liquid component to a mixing chamber 115. According to one preferred embodiment, the needle section 540 also comprises a valve 545 to inhibit the flow of liquid through the needle section 540.

In operation of this embodiment, an ampule 410 is placed inside of the chamber 515 of the base 510. The protective sleeve 520 is placed over the tip 416 of the ampule 410. Preferably with the sleeve 520 and tip 416 in one hand and the base 510 and body 412 in the other hand, the physician breaks the ampule tip 416 from the ampule body 412. The cap 530 is then placed over the body 412 of the ampule 410, and the cap 530 and base 510 are connected with each other. Preferably the cap 530 and base 510 are press fit with each other, however, one skilled in the art will understand other suitable means for connecting the cap 530 and base 510. The liquid component delivery system 500 is then inverted so that liquid component may flow by gravity into the needle section 530. The liquid component delivery system 500 is then connected to a port 140 in flow communication with a mixing chamber 115 to deliver liquid component to the mixing chamber 115.

It is therefore intended that the foregoing detailed description be regarded as illustrative rather than limiting, and that it be understood that it is the following claims, including all equivalents, that are intended to define the spirit and scope of this invention.

INDUSTRIAL APPLICABILITY

The system and method answers a long felt need for increasing safety and control in the mixing and administration of curable material to a patient by providing a closed mixing and delivery device wherein material may be dispensed directly from a mixing chamber. The mixing chamber includes a collapsible mixing element that mixes the components of the curable material and collapses within the mixing chamber as a plunger forces cement outside of the mixing chamber.

What is claimed is:

1. A device for mixing two components and dispensing a mixture comprising: a mixer section defining a mixing chamber having a first end and a second end; a mixing element holder at the first end of the mixing chamber wherein the mixing element holder defines a passageway between the mixing chamber and the exterior of the mixing chamber; a collapsible mixing element connected with the mixing element holder and operative to mix a first component and a second component within the mixing chamber; and a plunger operative to substantially seal against an interior surface of the mixing chamber wherein the collapsing mixing element collapses at the first end as the plunger is advanced from the second end to the first end, and the mixture is dispensed through the passageway in the mixing element holder.

2. The device of claim 1 wherein the collapsible mixing element is a spring.

3. The device of claim 1 wherein the mixer section defines a reduced diameter section proximal to the first end of the mixing chamber and at least a portion of the mixing element holder is positioned within the reduced diameter section.

4. The device of claim 1 wherein the mixing chamber defines a longitudinal axis and the collapsible mixing element is operative to mix the first component and the second component by rotating around the longitudinal axis.

5. The device of claim 1 wherein the plunger is connected to an injector having a handle and the plunger advances in the mixing chamber by rotating the handle.

6. A device for mixing two components comprising: a mixing barrel defining a mixing chamber; a liquid component introduction port on the mixing barrel for introducing a liquid component into the mixing chamber; a spring holder within the mixing chamber; a spring connected with the spring holder operative to rotate about a longitudinal axis of the mixing chamber wherein the spring is the only means for substantially mixing the liquid component and a powder component within the mixing chamber.

7. The device of claim 6 wherein the spring holder defines a passageway between the mixing chamber and the exterior of the mixing chamber.

8. The device of claim 7 wherein mixing of the first component and second component forms a curable material and the passageway is operative to dispense the curable material.

9. The device of claim 8 further comprising a plunger operative to substantially seal against an interior surface of the mixing chamber wherein the spring collapses at an end proximal to the spring holder as the plunger is advanced from the end distal to the spring holder to the end proximal to the spring holder.

10. The device of claim 9 wherein the plunger is connected with an injector having a rotatable handle and the plunger advances in the mixing chamber by rotating the handle.

11. The device of claim 6 wherein the mixing barrel is transparent.

12. The device of claim 6 wherein liquid component is delivered through the liquid component introduction port by a liquid delivery device comprising: an ampule containing a volume of liquid; an elongated ampule holder having a longitudinal axis and having a chamber operative to hold the ampule; at least one breaker pin slidably received within an opening of the ampule holder wherein rotational movement of the ampule holder causes the breaker pin to move radially inward and pierce the ampule.

13. The device of claim 6 wherein liquid component is delivered through the liquid component introduction port by a liquid delivery device comprising: an ampule containing a volume of liquid, the ampule at least partially broken; a base; and a cap removably attached to the base, the cap and base defining a chamber operative to hold the ampule, the cap having an output end for dispensing the liquid.

14. A device for mixing two components to form a mixture comprising: a mixer section defining a mixing chamber; a collapsible mixing element holder within the mixing chamber wherein the collapsible mixing element holder defines a passageway between the mixing chamber and the exterior of the mixing chamber; a collapsible mixing element connected to the collapsible mixing element holder operative to rotate about a longitudinal axis of the mixing chamber; and a drive shaft operative to engage the passageway of the collapsible mixing element holder wherein rotation of the drive shaft causes rotation of the collapsible mixing element holder.

15. The device of claim 14 wherein the collapsible mixing element is a spring.

16. The device of claim 14 further comprising a plunger operative to substantially seal against an interior surface of the mixing chamber wherein the collapsible mixing element collapses at an end proximal to the mixing element holder as the plunger is advanced from the end distal to the mixing element holder to the end proximal to the mixing element holder.

17. The device of claim 16 wherein the plunger is connected with an injector having a rotatable handle and the plunger advances in the mixing chamber by rotating the handle.

* * * * *